United States Patent [19]

Huggins

[11] 3,999,552
[45] Dec. 28, 1976

[54] EPILATOR

[75] Inventor: William H. Huggins, Clinton, Conn.

[73] Assignee: Universal Technology, Inc., Woodbridge, Conn.

[22] Filed: May 20, 1975

[21] Appl. No.: 579,148

[52] U.S. Cl. .................. 128/303.13; 128/303.17
[51] Int. Cl.² ................................. A61N 3/04
[58] Field of Search .......... 128/308.13, 303.14, 128/303.17, 303.18, 404, 405, 413, 422

[56] References Cited

UNITED STATES PATENTS

| | | | |
|---|---|---|---|
| 2,888,927 | 6/1959 | Fozard | 128/303.13 |
| 3,100,489 | 8/1963 | Bagley | 128/303.17 |
| 3,315,678 | 4/1967 | Donelson | 128/303.18 |
| 3,707,149 | 12/1972 | Hao et al. | 128/303.17 |
| 3,800,802 | 4/1974 | Berry et al. | 128/422 |
| 3,875,945 | 4/1975 | Friedman | 128/303.17 |

FOREIGN PATENTS OR APPLICATIONS 166,452   8/1962   U.S.S.R. .......... 128/303.17

*Primary Examiner*—Robert W. Michell
*Assistant Examiner*—Lee S. Cohen
*Attorney, Agent, or Firm*—DeLio and Montgomery

[57] ABSTRACT

An epilator comprising a radio frequency signal generator, a high impedance hair gripper, and a shielded transmission line therebetween. The transmission line has a length of 0.15 to 0.50 of a quarter wave length greater than an odd quarter wave length of the signal considering the velocity factor of the line, and a variable impedance matching network is disposed between the signal generator and the gripper.

3 Claims, 4 Drawing Figures

EPILATOR

This invention relates to epilators, and more particularly relates to epilators of the type in which the hair to be removed is grasped and slid from the follicles.

For many years the removal of superfluous hair by high-frequency coagulation of the root required a needle to be inserted into the follicle containing the unwanted hair. The needle is energized by high frequency electrical energy which coagulates the hair papilla and thus kills the hair root, after which the hair could be plucked from the follicle. This is a very time-consuming process and problems are presented in that even a skilled operator may cause a burn or cut by the needle. Moreover, the insertion of the needle is painful, particularly in tender spots such as a nostril, or the like, when it is attempted to remove a hair therefrom.

Another type of epilator is disclosed in U.S. Pat. No. 2,888,927 wherein the hair to be removed is gripped by a gripping means connected to a high frequency generator and high frequency energy is supplied thereto. The hair is gripped in spaced relation to the skin. When the gripping means is energized the hair root is coagulated, after which the hair can be readily removed without pain. In this type of device the hair is gripped in spaced relation to the skin and there is no necessity to insert any instrument into the follicle.

However, in this type of device as well as in the needle type of device, a problem is presented by the radiation of high frequency energy from the line connecting the generator and the needle or gripping device, and also the efficient transfer of power to the papilla. A large amount of power may be required due to such radiation. Generally, all epilators operate at an FCC frequency set aside for medical use, and there are certain requirements governing the maximum permissible radiation.

Briefly stated, the invention in one form thereof comprises the provision of a shielded transmission line between the hair gripping device and the generator together with an adjustable impedance network between the line and the generator. The line which is essentially pure capacitive impedance has a low characteristic impedance, while the gripping means has a much larger impedance. To provide optimum transfer of energy to the transmission line, the effective length of the line is between 0.15 and 0.50 of a quarter wave length greater than an odd quarter wave length of the line considering the velocity factor of the line.

An object of this invention is to provide a new and improved epilator.

Another object of this invention is to provide an epilator of the gripper type where power is more efficiently transferred to the hair papilla, and without undue radiation of radio frequency energy.

The features of the invention which are believed to be novel are particularly pointed out and distinctly claimed in the concluding portion of this specification. However, the invention both as to its operation and organization together with further objects and advantages thereof may best be appreciated by reference to the following detailed description taken in conjunction with the drawings, wherein:

Figure 1:
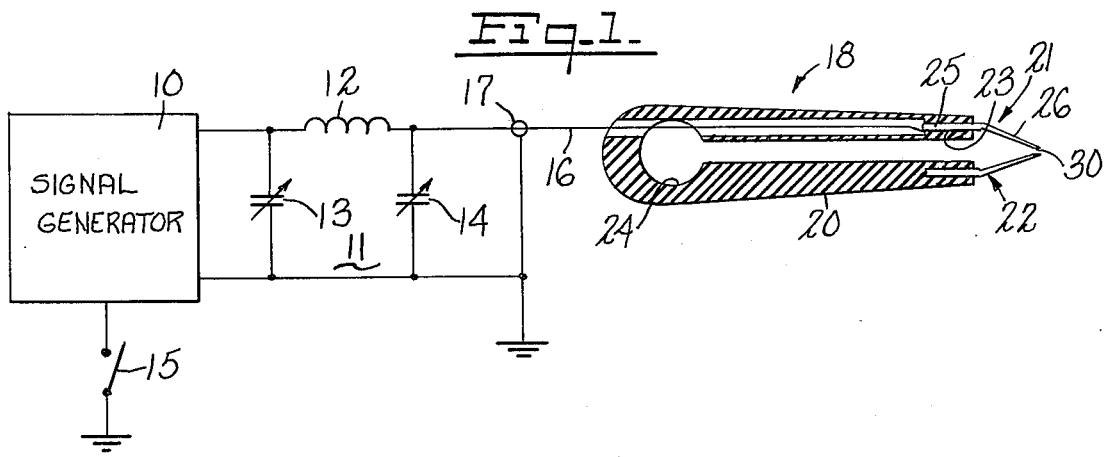
FIG. 1 is a view, partly schematic and partly in block form of apparatus embodying the invention.

As shown in FIG. 1, apparatus embodying the invention comprises a radio frequency (RF) signal generator or oscillator 10 which may be designed to operate at various frequencies. However, due to Governmental regulatory purposes it is designed to operate at a Federal Communications Commission (FCC) medical frequency of 27.120 megahertz.

One form of the signal generator comprises an oscillator having a 6146 pentode, a rectifier, a 27.120 megahertz crystal and 5763 pentode. The above-mentioned components, which are not shown, are arranged in a conventional manner. The signal generator further includes an impedance matching network 11 comprising a series inductance 12 and parallel capacitors 13 and 14 in a pi network. A switch 15, which may be a foot pedal operated switch, either connects or disconnects operating power to the output stage of the signal generator. A shielded cable 16, preferably in the form of a coaxial cable with the outer conductor 17 grounded, is connected to a hair gripping device 18. The other end of line 16 is connected to a coaxial cable plug-type connector which is received in a female receptacle on a housing for generator 10 and network 11.

The gripper 18 comprises a cast or molded plastic generally U-shaped flexible body member 20 having metallic gripping fingers 21 and 22 adapted to grasp a hair. At least finger 21 is metallic and connected to line 16. The inner conductor of cable 16 is placed in contact with a flat portion 23 of finger 21. Member 20 acts as a tweezer due to flexibility of portion 24. The shielding outer conductor is continued over portion 25 of finger 21 and angled portion 26 acts as an antenna.

Figure 2:
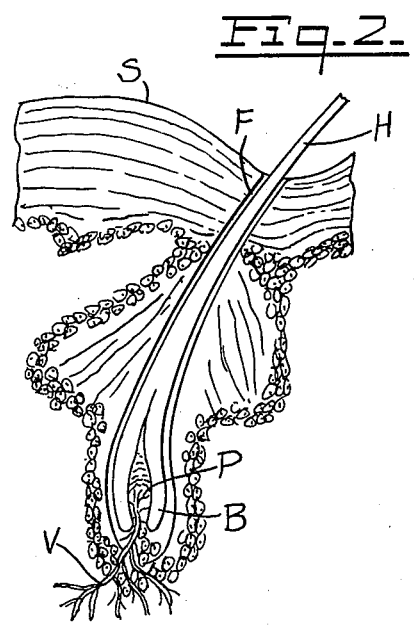
FIG. 2 is a representation of a cross-section of a human hair in the skin.

Reference is made to FIG. 2 which exemplifies a human hair H, extending from a follicle F. Human hair is made of a protein called keratin. It is not a conductor of RF energy. The disclosed epilator uses the hair as a dielectric material to transfer RF energy to the papilla P. If properly applied the RF energy causes coagulation of the papilla thus preventing regrowth.

The hair consists of two portions, the shaft and the root. The hair shaft is the portion extending beyond the surface of the skin S. The hair root is the part beneath the skin surface. At the lower extremity of the hair root is found a bulbous portion known as the hair bulb B which fits over the papilla P. Nourishment reaches the hair through the papilla. Blood vessels V supply the papilla with nourishment for growth. Only when the papilla has been decomposed, or the follicle destroyed by injury or disease, will the hair fall out and not be replaced. The follicle F is a tube-like depression of the skin, from which the hair emerges.

Figure 3:
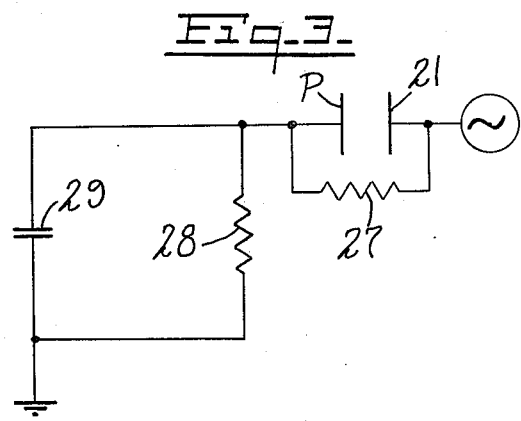
FIG. 3 is a schematic diagram of an electrical circuit including the apparatus of FIG. 1 and an electrical representation of the hair of FIG. 2.

FIG. 3 represents an electrical schematic of the device together with an electrical representation of the hair and body. When the hair is gripped by the gripper the energized finger 21 acts as one electrode of a capacitor. The second electrode of the capacitor is the papilla P. The dielectric of the hair is represented by the resistance 27 between capacitor electrodes 21 and P and the resistance-capacitance network 28 and 29 represents the human body.

When the gripper is energized from the signal generator 10, RF energy is dissipated in the capacitor comprising the gripper, the hair and the papilla causing coagulation of the papilla. Very little of the RF is lost along the shank of the hair because of the hair-to-air-to-skin interface in the follicle.

It has been found that a problem may be presented in the transfer of energy from the signal generator to the tip 30 of finger 21. In some cases little of the original frequency is transmitted, and various harmonics and sub-harmonics of the generated frequencies are radiated.

The cable 16 of the coaxial type has a relatively low characteristic impedance and is seen solely as a capacitance by signal generator 10. The gripper finger 21 contacted by the active conductor of the cable has an impedance which is substantially higher than the characteristic impedance of line 16 and therefore will produce an impedance mismatch, and transfer very little power to the papilla if certain conditions are not observed. For example, it is desired to provide essentially a standing wave on the transmission line when a hair is not gripped and the line is open.

The length of a one-quarter wave transmission line to produce a standing wave in free space at a frequency of 27.120 megahertz is $$\frac{\lambda}{4} = \frac{1}{4}\left(\frac{3 \times 10^6}{27.12 \times 10^4}\right) = 9.08 \text{ ft.} \quad (1)$$

The length of a practical one-quarter wave length transmission line is $$\frac{\lambda}{4} = \frac{2.46 \times 10^6 V}{27.12 \times 10^4} = 5.99 \text{ ft.} \quad (2)$$

and where V is the velocity factor on the transmission line and may be considered equal to 0.66 for RG-58/U cable selected.

However, it has been determined that in the instant situation where the impedance of the gripper is substantially greater than the characteristic impedance of line 16 the foregoing equation is not valid.

I have determined that for effective transfer of power at the gripper without undue radiation from the gripper, the length of the line 16 must be substantially 0.15 to 0.50 of a quarter wave length greater than an odd quarter wave length of the line 16 and preferably 0.30 to 0.35 of a quarter wave length greater than an odd quarter wave length of the line, considering the velocity factor of the line.

Figure 4:
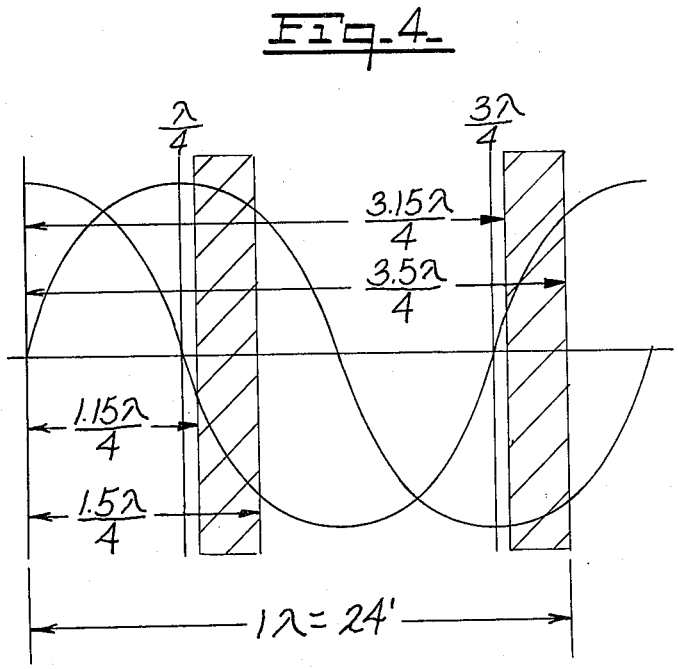
FIG. 4 is a waveform diagram of the wave appearing on the transmission line of FIG. 1.

Reference is now made to FIG. 4 which shows the relationship of current and voltage on the line 16 when it is open ended. The wave length is considered, for purposes of example, to be twenty-four feet from equation (2). It will be noted that at the quarter-wave lengths the current wave is zero. At distances slightly more than the odd one-quarter wave lengths there is both a voltage and a current value. It is at these lengths of the line 16 that adequate power is transferred to the papilla of the hair to coagulate or decompose it. I have found that when a line 16 is utilized which is between an odd number of quarter wave lengths of the frequency plus 0.15 – 0.50 of the quarter wave length considering the velocity factor, the papilla is efficiently coagulated with minimum power requirements and radiation.

It will be noted from FIG. 4 that the critical ranges 1.15 $\lambda/4$ to 1.5 $\lambda/4$ and 3.15 $\lambda/4$ to 3.52 $\lambda/4$ occur as the voltage is falling from a maximum and there is some current value. This provides both sufficient driving voltage and power to coagulate the papilla.

It will of course be most practical to use a line 16 of one quarter wave length plus 0.15 to 0.5 of the quarter wave length at the frequency discussed.

It has been determined that the ideal length of the line 16 in the example given for RG-58/U cable should be 8.0 feet which is 1.33 of a quarter wave length of the frequency utilized.

In FIG. 4 the shaded zones represent the acceptable transmission line lengths.

At this dimension of the line 16, it is found that by varying the impedance of matching circuit 11, the maximum power will appear at the end of gripper member 21 with very little undesired radiation.

The impedance matching network 11 is adjusted until there is maximum energization of a small neon bulb placed in contact with gripper finger 21. A one-quarter watt NE51 bulb is suitable.

It is believed that the reason for the discrepancy in the calculated length of line 16 and the most efficient length is that it is required to move the standing wave slightly along the voltage curve to provide proper impedance matching and power transfer. Therefore, to be able to couple any gripper to the generator, a variable means must be provided to control output matching impedance and power transfer. The pi network 11 has been found to be the most efficient and economical. However, other impedance matching networks may be utilized.

The gripper and cable must be treated essentially as a one-quarter wave transmission line with an open circuit at the gripper end. It is extremely difficult to determine the actual impedance of the gripper at the frequencies utilized but measurements of various grippers have shown the impedance to be somewhere between 600 and 1000 ohms. The signal generator output must match a load comprising a line of relatively low characteristic impedance and a termination at the gripper of a relatively high impedance, to provide adequate power transfer.

In a one-quarter wave open-ended transmission line there is a maximum voltage and a zero current point. In normal applications a standing wave developed on this type of line is intolerable. However, I have found in this particular application the production of the standing wave is an essential requirement. To determine that maximum power transfer will occur, the end of the gripper is contacted to the connections of the neon bulb indicator previously described. The signal generator is energized by closing switch 15, and the impedance matching network 11 is varied through the capacitors 13 and 14 to provide maximum energization of the neon bulb. At this time, it is known that essentially a standing wave exists on the transmission line 16. These adjustments are done at the factory. Thereafter the user makes no adjustment.

In actual operation, the gripper fingers 21 and 22 grasp a hair in spaced relation to the skin and the hair is pulled back to open the follicle, and the hair brought back to the normal position. The switch 15 is closed and RF energy is transmitted to the moist area of the bulb B and papilla P. The RF energy is dissipated in the capacitor described in conjunction with FIG. 3, causing coagulation of the papilla. Uniform tension is applied to the hair during the foregoing treatment, then the hair is slid out of the follicle.

It may thus be seen that the objects of the invention set forth as well as those made apparent from the foregoing description are efficiently attained. While preferred embodiments of the invention have been set forth for purposes of disclosure, modification to the disclosed embodiments of the invention as well as other embodiments thereof may occur to those skilled in the art.

Accordingly, the appended claims are intended to cover all embodiments of the invention and modifications to the disclosed embodiments which do not depart from the spirit and scope of the invention.

What is claimed is:

1. In an epilator comprising means for generating a radio frequency signal and a metallic hair gripping means for gripping a hair in spaced relation to the skin connected to said generating means, the improvement comprising a shielded transmission radio frequency line connected between the output of said generating means and said gripping means having a length between 0.15 and 0.50 of a quarter wave length greater than an odd quarter wave length of said line considering the velocity factor of said line.

2. The epilator of claim 1 wherein said line has a length between 0.30 and 0.35 of a quarter wave length greater than an odd quarter wave length of said line considering the velocity factor of said line.

3. The epilator of claim 1 wherein said line has a characteristic impedance, said gripping means has a substantially greater impedance than said characteristic impedance, and an adjustable impedance matching network is provided between said generating means and said line.

* * * * *